Figure 1:
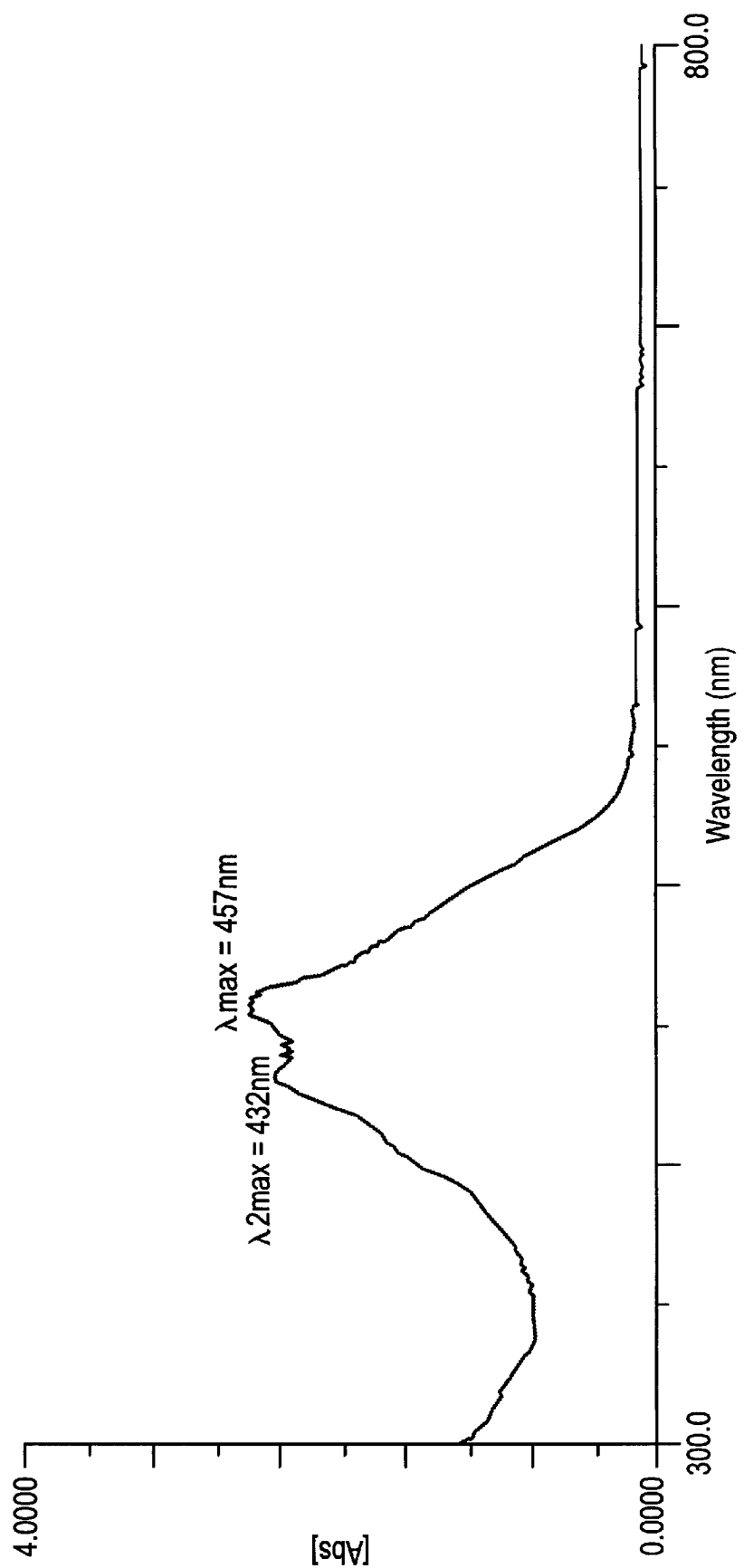

United States Patent
Collin

Patent Number: 6,055,936
Date of Patent: May 2, 2000

[54] SEA CUCUMBER CAROTENOID LIPID FRACTIONS AND PROCESS

[76] Inventor: Peter Donald Collin, P.O. Box 172, Sunset, Me. 04683

[21] Appl. No.: 09/010,123

[22] Filed: Jan. 21, 1998

Related U.S. Application Data

[60] Provisional application No. 60/035,940, Jan. 21, 1997.

[51] Int. Cl.[7] .................................................. A01K 61/00

[52] U.S. Cl. ............................. 119/215; 554/18; 424/548

[58] Field of Search .............................. 554/18; 424/548; 119/215

[56] References Cited

PUBLICATIONS

Findlay et al., Frondogenin, A New Aglycone From the Sea Cucumber *Cucumbaria frondosa*. *Journal of Natural Products*, Mar.–Apr. 1984, vol. 47, No. 2, pp. 320–324.
Search Report.

*Primary Examiner*—Deborah D. Carr
*Attorney, Agent, or Firm*—Rothwell, Figg, Ernst & Kurz, P.C.

[57] ABSTRACT

Processing methods and compositions of matter are disclosed for lipid fractions of sea cucumber intestinal mass and body wall tissue suitable for the healthfood industry and aquaculture feed pigment industry. A process and composition of matter description for obtaining a high protein de-lipidized, de-odorized meal is also disclosed.

13 Claims, 2 Drawing Sheets

SEA CUCUMBER CAROTENOID LIPID FRACTIONS AND PROCESS

This application claims the benefit of copending provisional application 60/035,940, filed Jan. 21, 1997.

FIELD OF THE INVENTION

The invention relates to processes for extraction of carotenoid-lipid fractions, especially canthaxanthin-bearing fractions, from the marine echinoderm, sea cucumber, and especially, the orange-footed sea cucumber, *Cucumaria frondosa*. Other lipid fractions are removed in conjunction with the same process which provide a novel source of the omega-3 fatty acids and tochopherols. Finally, the process produces an odorless, tasteless protein meal.

BACKGROUND AND PRIOR ART

Aquaculture is now a major industry in the United states and the world. Many species grown in artificial environments require the addition of carotenoids to their diets, especially astaxanthin and canthaxanthin. It has been thought by those familiar in the industry that carotenoids natural to the species' environment are preferable to synthetic pigments. The production of natural carotenoids from natural sources such as phaffia yeast and marine microbial algae and crawfish shell address this industry need for natural pigments.

It is also of importance to find economically feasible means to dispose of various pigment bearing waste streams such as those of crawfish, crab, and now, sea cucumber gut material. Because the sea cucumber gut material is now known to be a rich source of usable pigments, there existed a potential to produce those isolated pigments and related lipid fractions from the sea cucumber industry waste materials provided that a method suitable for a large-scale operation could be found.

Carotenoids from sea cucumbers have been mentioned in various scientific journal articles, to wit:

Matsuno, et al reported the occurrence of astaxanthin as the major carotenoid in the gonads of the sea cucumbers *Holothuria leucospilota* and *Stichopus japonicus*, and beta carotene, echinenone, canthaxanthin and zeaxanthin were identified from the gonad of *H. leucospilota* and *S. japonicus*. On the other hand, astaxanthin and the esters, canthaxanthin, phoenicoxanthin, and ochincnone, were isolated by Bullock and Dawson from the red body wall of *Psulus fabrichii*. M. Tsushima, et al reported on the novel marine di-Z carotenoids, cucumariaxanthins A, B and C from the Sea cucumber *Cucumbaria japonica*. J. Findlay, et al reported on canthaxanthin from the species, *Cucumaria frondosa*. None of these reports provide any means whereby to utilize such carotenoids for any aquaculture or medical or healthfood industry, and none provide methods to concentrate such pigmented lipid fractions.

The U.S. Pat. No. 4,692,280 by Spinelli, Stout, and Nilsson describe a method for obtaining purified fish oils using supercritical carbon dioxide, and is included herein by reference. This patent does not disclose a means of obtaining sea cucumber lipid fraction purification through the supercritical purification methodologies set forth in the patent. U.S. Pat. No. 4,495,207 provides a method of extracting lipids from corn germ. Essentially the same methodologies were used by the inventor to extract lipids from sea cucumber tissue as is set forth in U.S. Pat. No. 4,495,207 and is included herein by reference.

Thus, there is no prior art for the efficient and large scale removal of lipid fractions, and non directed at obtaining usable carotenoid or non carotenoid lipid fractions of sea cucumber tissue.

OBJECTS OF THE PRESENT INVENTION

It is an object of the present invention to provide a means to recover usable pigmented lipid fractions and pigment-free lipid fractions from the intestinal gut material, and body wall from sea cucumbers, especially from the species *Cucumaria frondosa*. It is a further object of the present invention to disclose a composition of matter which is the pigmented lipid fraction and a de-pigmented lipid fraction resulting from such means of recovery. The resultant pigmented lipid fraction contains approximately 600 to 5,000 parts per million of carotenoid and is useful in the aquaculture industry as a feed ingredient. The resultant non-pigmented lipid fraction contains vitamin E and Omega-3 fatty acids heretofore unknown in the marine oil sciences, and is useful as a topical application in mammals in need of such fatty acids, or encapsulated into soft gel capsules suitable for human consumption. The dry, proteinaceous meal is high in protein and polysaccharides and is suitable for inclusion in animal feeds as a source of protein and minerals.

THE INVENTION

These and other objects are accomplished in accordance with the present invention embodying a process, the steps of which include, in combination:

a. Separating gut material from the processed sea cucumber by hand or machine. Hand separating involves cutting the animal with a knife and physically removing the intestines. Machine cutting involves any mechanized embodiment wherein automated cutting tools are able to cut open the animal whereby the intestines are available for removal.

b. The proteinaceous/lipid gut material is pretreated after separation from the animal with sufficient acid to lower the pH of the material to within a range of from about 4 to about 5.5 preferably about 4.3 to about 4.7 to suppress microbial degradation, demineralize the mass and improve overall red carotenoid pigment recovery during the subsequent extraction with solvent or combinations of solvents.

c. In one method of processing, the proteinaceous/lipid gut material is mixed with acetone, alcohol or similar solvent in 3:1 solvent to material ratio and then agitated, for 24 hours or until sufficient pigment has released from the gut material to the solvent.

d. The acetone or other solvent is decanted off of the remaining gut material and the gut material is washed subsequently four or more times with clean solvent to remove remaining carotenoids.

e. The remaining gut material is centrifuged to purge remaining solvent, or heated in a closed vessel and the solvent reclaimed by methods known to those in the arts.

f. The pigment bearing acetone or solvent is pumped to a 'wiped film evaporator' as is known in the oil chemists' arts and the pigment is retained and sequestered and the solvent is reclaimed.

g. The resultant lipid pigment fraction is a mixed carotenoid of canthaxanthin, cucumariaxanthin, astaxanthin, and zeaxanthin. The major carotenoid is canthaxanthin in the example of *Cucumaria frondosa*.

h. The resultant pigmented lipid fraction can be stabilized with known antioxidants as are known in the arts.

g. The remaining gut material is then dried and extracted with hexane, butane, supercritical carbon dioxide, or similar solvent to remove a golden oil essentially free of pigments. The resultant remaining dry proteinaceous material free of lipids is high in protein and polysaccharides and is suitable for inclusion into animal feeds. This proteinaceous de-lipidized meal is unique in the marine fish-meal industry inasmuch as it is both de-pigmented, de-lipidized, is high in usable protein, and is essentially free of odoriferous contaminants. It is easily manufactured into powder.

In another embodying process of the present invention, the separated sea cucumber guts are dried after being acidified as described in the previous method. The drying process can be low (60–80 F.) heat or higher heat (150–200 F.) without effecting the target lipid fractions or carotenoids. This embodying process which includes drying the gut material is further accomplished by steps which include, in combination:

a. Subjecting the dried gut material which has a moisture content of less than approximately 10% to a standard "oil-recovery procedure" with hexane or other suitable solvent known to those skilled in the arts, wherein the dry gut material is mixed at 1:1 ratio at 130 F. for 5 minutes and then drained. The extracted product is then washed three times with fresh solvent. The solutions containing the carotenoid is desolventized in a wiped film (Luwa and Pope) evaporator at 95 C. and 28 inches Hg vacuum.

b. Sequestering the solvent/lipid phase into containers designed for such use and freeing said solvent/carotenoid mixture from carotenoid oil phase by standard "steam stripping" or by "wiped film" oil technology.

c. Treating such oil phase with anti-oxidants which are known to those skilled in the arts such as 6-ethoxy-1,2-dihydro-2,2,4-trimethylquinoline (Ethoxyquin, Monsanto) at between 300 to 600 parts per million or vitamin E at approximately 1 percent.

d. Subjecting the red pigmented oil thus obtained to a degumming process by the addition of 1% water to the oil then allowing to hydrate for 30 mintes and then centrifuging at 8000 rpm at 150 F.

e. Recovering the concentrated pigment in the following manner:

The degummed oil is first pretreated with 0.5% silica gel (Trysil 600, Grace Co.), heated to 180 F. and then filtered out using 6 micron filter paper. The recovery of the color is conducted by adding 5 percent bleaching (activated) clay (Englehard 105) to the pretreated oil and the oil is then heated to 220 F. for 20 minutes at 28 in Hg of vacuum. The resulting oil is light yellow color and most of the pigment is adsorbed in the bleaching clay. The resulting clay is then extracted with acetone 1:2 clay to solvent ratio and washed twice. The resulting solution is then desolventized in an evaporator (Rotovap) at 90 C. and 29 in Hg vacuum.

f. Determining the carotenoid content of extracted concentrate by standard HPLC methods known to those skilled in the arts. Concentrated pigment extracted by this present invention is suitable for inclusion in aquatic diets and contains parts per million of carotenoids canthaxanthin at between 2,000 and 5,000, depending on the carotenoid content of the original material.

g. Stabilizing de-pigmented lipid from the carotenoid extraction procedure by the addition of vitamin E or other suitable antioxidants known to those in the arts, at between 1 and 5% by weight.

h. Encapsulating de-pigmented lipid fraction from the carotenoid extraction procedure of sea cucumber intestinal mass subsequently in "soft-gel" capsules of 500 to 1000 milligrams, or packaging into suitable containers for oral and topical administration to mammals. Topical administration products can be obtained by any combination of emollients combined with the non-pigmented lipid fraction, depending on desired effect in a specific or general condition.

g. Incorporating said pigmented lipid fraction, depending upon parts per million of carotenoid, into aquatic diets at a percentage of such food sufficient to produce carotenoid deposition into flesh or skin.

It is an object of the present invention to disclose a composition of matter comprising a carotenoid lipid fraction obtainable from sea cucumber gut material which contains varying percentages and parts per million, depending on environmental factors, of astaxanthin, and canthaxanthin. One of the carotenoid lipid fraction so disclosed was determined to contain 4,706.52 parts per million of canthaxanthin by spectrophotometric analysis. The chromatograph is attached hereto as FIG. 1. FIG. 1 shows a chromatogram which was obtained from a Beckman DU-800 Chromatograph of the acetone extracted carotenoid lipid fraction of fresh sea cucumber gut material having a calculated ppm of 4,706.52 carotenoid content. Twenty three milligrams of acetone extracted carotenoid lipid fraction was diluted with 10 ml of petroleum ether with an extinction coefficient of E=2400, and read at 467 nm for canthaxanthin.

It is a further object of the present invention to disclose a composition of matter comprising the sea cucumber gut lipid fraction essentially free of carotenoids. This non-pigmented lipid fraction is unique and hitherto not described in the literature. It is relatively odorless; contains significant amounts of the omega 3 fatty acid, EPA (Eicosapentanoic acid); and contains vitamin E.

Figure 2:
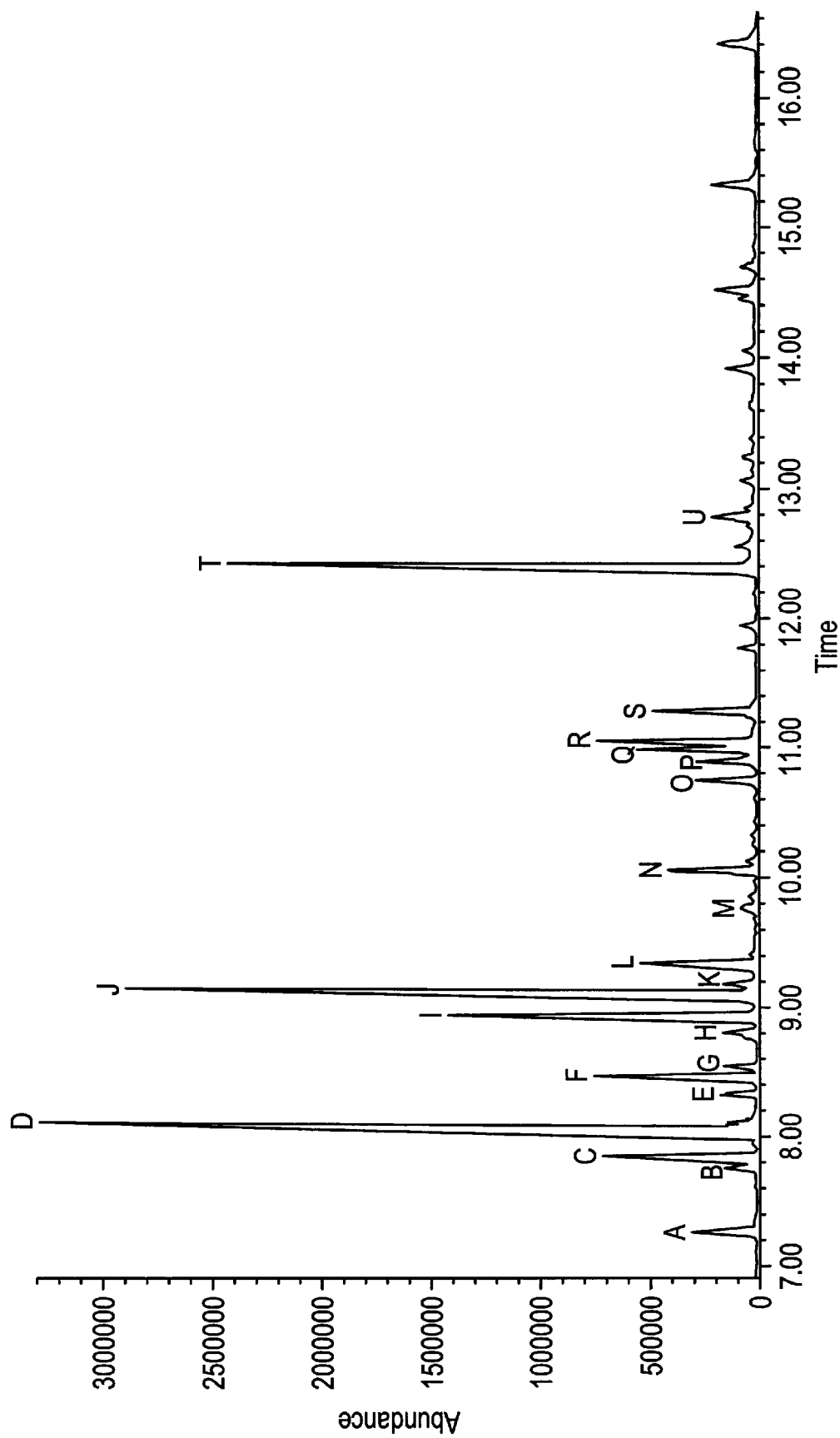

The Gas Chromatograph and Mass spectrometer data appears in FIG. 2. FIG. 2 is the GC/MS of the de-pigmented lipid fraction after extraction of carotenoids by the means of activated clay transference, and was performed with High Pressure Liquid Chromatograph analysis (HPLC). The HPLC was carried out according to Vecchi and Muller (1979) on a Dupont 830 LC equipped with a Varian 634-detector at 481 nm, at ca 1200 psi, column Spherisorb S-5CN, hexane/isopropyl acetate/acetone 76:17:7 as mobile phase, flow 1.5 ml/min. The de-pigmented lipid fraction was first saponified to free fatty acids using sodium methoxide, as is standard in the lipid analytical arts, and then acidified, and then converted to methyl esters. Subsequent synthetic metheyl esters thus produced were compared to standard profiles of fatty acids from known reference libraries. Table 1 compares the percentage of match of the fatty acids from the sea cucumber de-pigmented lipid fractions with known fatty acid profiles.

TABLE 1

| Peak | Compound from Library | % Match |
| --- | --- | --- |
| A | tetradecanoic acid, methyl ester | 97 |
| B | 2-nathol, 8-amino | 64 |
| C | pentanamide | 49 |
| D | pentadecanoic acid, methyl ester | 91 |
| E | pentadecanoic acid, methyl ester | 98 |
| F | hexadecanoic acid, methyl ester | 43 |
| G | pentadecanoic acid, 4-methyl-, m.e. | 64 |
| H | hexadecanoic acid, methyl ester | 41 |
| I | hexadecanoic acid, m.e. | 87 |
| J | 7-hexadecanoic acid, m.e. | 99 |
| K | 9-hexadecanoic acid, m.e. | 98 |
| L | pentadecanoic acid, 14-methyl-, m.e. | 93 |
| M | hexadecanoic acid, 14-methyl-, m.e. | 93 |

TABLE 1-continued

| Peak | Compound from Library | % Match |
|---|---|---|
| N | hexadecanoic acid, 15-methyl-, m.e. | 78 |
| O | 1,2,8-dodecatriene, (E,E,E)- | 94 |
| P | 10,13-octadecadienoic acid, m.e. | 98 |
| Q | 9-octadecenoic acid (Z)-, m.e. | 99 |
| R | 7-octadecenoic acid, m.e. | 99 |
| S | octadecanoic acid, m.e. | 98 |
| T | methyl eicosa-5,8,11,14,17-pentaenoate | 80 |
| U | 7-hexadecenoic acid, m.e. (Z) | 91 |

It is a further object of the present invention to disclose a composition of matter comprising the sea cucumber gut material which has been de-lipidized through the method herein described. This material is unique inasmuch as it is essentially free of odor, high in protein, and is easily made into useable powder. The two examples which immediately follow are illustrative of typical runs selected from a number of runs made using the differing techniques and solvents. Body wall tissues once dry, contain extractable lipid fractions, and the inventor has sequestered same by means similar to those herein described. The lipid fraction content of body wall tissues is much less, however, than gut material, at about 1 to 2% of total dry weight of body-wall tissue.

Fresh sea cucumber gut material from *cucumaria frondosa* was also shown by the inventor to be extractable with hot edible oil as per method of Meyers and Chen (Extraction of Astaxanthin Pigment from Crawfish Waste Using a Soy Oil Process, Journal of Food Science; Vol. 47, 1982). U.S. Pat. No. 4,505,963, also of Meyers and Chen, discloses an industrial means whereby crawfish carotenoid pigments are extracted from processing waste utilizing hot oil. Although the applicability of this industrial method differs in various ways from a 'hot oil' method possible using fresh sea cucumber gut material as a primary resource, the process is essentially the same. U.S. Pat. No. 4,505,963 is includes herein by reference.

EXAMPLE 1

One hundred pounds of fresh sea cucumber gut material was mixed with approximately fifty-five gallons of acetone and agitated at room temperature for three house in a 300 gallon closed vessel. The acetone was drained from the mixture into a containment vessel and fresh acetone was washed over the gut material until little pigment color was obtained. The acetone was pumped through a wiped film evaporator (Pope Still) and the water included in the acetone mixture and the acetone was separated from the pigmented lipid fraction and re-claimed. The acetone was salvaged and the water phase was discarded.

The resulting lipid fraction (0.63 pounds) had a heavy grease consistency and 4,700 parts per million of the carotenoid canthaxanthin. The antioxidant, 6-ethoxy-1,2-dihydro 2,2,4-trimethylquinoline (Ethoxyquin, Monsanto) was added to the lipid phase and mixed at 1% by weight.

The heavy lipid fraction containing carotenoid material (Red Grease) was determined to contain 4,700 parts per million of canthaxanthin by HPLC analysis and was incorporated into standard ornamental fish feed which had had the commercial carotenoid material removed. The fish feed contained 80 parts per million "Red Grease material." Clownfish were fed an experimental diet of this feed for two months and were judged by a panel of 5 judges giving an average number score of 8.5 (on a scale from 1 to 10, with '10' being a very acceptable color deposition), to have deposed acceptable color to their skin.

EXAMPLE 2

Sea cucumbers (1000) of the species *Cucumaria frondosa* were eviscerated by hand and the gut material (352 pounds) was dried by low heat means at 70 degrees F. for 4 days in a seafood dryer (Southwind, Nova Scotia). Prior to drying, Propionic acid was added to the fresh, wet sea cucumber gut material at 7.2% by weight. The resultant dried material (105 pounds) contained 10% moisture and 51% lipids. The dry gut material was then subjected to hexane extraction of the lipid fraction as per industry standards in a 200 gallon closed vessel, essentially the same process used in the soybean oil industry, and a red lipid fraction (42 pounds) containing 824.5 parts per million carotenoid judged as canthaxanthin with 8.8% eicosapentanoic fatty acid was produced. This lipid fraction also contained 35 IU d-alpha tochopherol per 100 grams. The red lipid fraction (oil) was then degummed by the addition of 1% water to the oil then allowing to hydrate for 30 minutes and then centrifuged at 8000 rpm at 150 F.

The degummed oil (sea cucumber gut lipid fraction) was first pretreated with 0.5% silica gel, heated to 180 F. and then filtered out using 6 micron filter paper. The recovery of the color was conducted by adding 5 percent bleaching clay to the pretreated oil. The oil was heated to 220 F. for 20 minutes at 28 in Hg of vacuum. The resulting oil (34 pounds) was light yellow color and most of the pigment was adsorbed in the bleaching clay. The resulting clay was then extracted with acetone 1:2 clay to solvent ratio and washed twice. The resulting solution was then desolventized in a Luwa evaporator at 90 C. and 29 in Hg vacuum and 8 pounds of red lipid fraction concentrate was recovered.

The process resulted in three materials; a yellow/gold oil; a concentrated red carotenoid-bearing lipid fraction; and a dry protein powder without lipids. The yellow lipid fraction was incorporated into a topical cosmetic and an oral "nutraceutical" marine "Omega 3 lipid" product. The red concentrated lipid fraction was incorporated into an ornamental fish diet for one month to determine the effectiveness of the carotenoid at producing suitable color to such fish.

Five Pearlgami ornamental fish were fed an experimental diet into which the sea cucumber concentrated pigment was added to produce a feed which contained 91 parts per million pigment. The fish were fed ad libitum for one month and were judged according to the acceptability of skin color deposition by a panel of 6 judges. Judges scores averaged 9.1 as per acceptability of the fish fed the experimental diet containing sea cucumber carotenoids.

EXAMPLE 3

The above extractions were also carried out using supercritical carbon dioxide as an extracting solvent as is known in the arts. These experiments obtained essentially the same lipid fractions as hexane and liquefied propane.

It is apparent that various modifications and changes can be made without departing the spirit and scope of the invention.

REFERENCES CITED

Novel Marine di-Z-Carotenoids: Cucumariaxanthins A, B, and C from the Sea Cucumber *Cucumaria japonica*. M. Tsushima, et al. J. Natural Prod. 1996, 59, 30–34

Goodwin, T. W. The Biochemistry of the Carotenoids, Vol. 11, Annuals, Chapman and Hall, London 1984

Matsuno, T. et al In Marine Biogenic Lipids, Fats and Oils: Ackman, Ed. CRC Press; Boca Raton Fla. 1989 Vol. 1

J. Findlay, et al, 1983

Matsuno, etc. al Experimentia 1969. 25, 1253

Matsuno, T. et all Experimental 1971, 27, 509

Matsuno, T. et al Bulletin Japan Soc. Sci. Fish 1971 37, 513–517

Bullock, E et al Comp. Biochem. Physiol. 1970, 34, 799–80

Having described the invention, What is claimed is:

1. A process for the large-scale extraction of usable lipid fractions from sea cucumber tissue comprising:
    a. extraction of guts of sea cucumber by hand or machine
    b. an acidifying step of a pH of between 4 to 5.5 of the sea cucumber gut material
    c. a step of drying the acidified sea cucumber gut material
    d. extracting total lipid fraction from acidified dry gut material by either hexane, liquefied propane, super-critical carbon dioxide, or combinations of the above.

2. The process of claim 1 further comprising the steps of extraction of carotenoid pigmented lipid fractions from total lipid fractions of sea cucumber gut material by the use of activated clay.

3. The process of claim 1 wherein the extraction is with liquid propane.

4. The process of claim 1 wherein the extraction is with super-critical carbon dioxide.

5. The process of claim 1 wherein the extraction is with hexane.

6. A process for the large-scale extraction of usable lipid fractions from sea cucumber tissue comprising:
    a. extraction of guts of sea cucumber by hand or machine,
    b. acidifying the guts to a pH between 4 and 5.5
    c. extraction of total carotenoid lipid fraction from the acidified sea cucumber guts with acetone or
    b. extraction of total sea cucumber carotenoid lipid fractions into an edible oil by a "hot oil" industrial process.

7. A method for pigmenting fishes in need of same by the inclusion of sea cucumber carotenoid lipid fraction into diets as an additional component of such diet.

8. A process of claim 7 for pigmenting fishes wherein the sea cucumber carotenoid lipid fraction is concentrated by the use of activated clay and acetone.

9. A method of obtaining a sea cucumber lipid fraction containing Omega-3 fatty acids and no carotenoids by:
    a. contacting sea cucumber carotenoid bearing lipid fraction with activated clay under vacuum and heat
    b. separating and extracting clay fraction with acetone to obtain concentrated carotenoid fraction
    c. separating clay/carotenoid fraction from remaining lipid fraction to obtain a carotenoid-free lipid fraction.

10. A composition of matter comprising a carotenoid lipid fraction obtained through acetone extraction of fresh acidified sea cucumber gut material.

11. A composition of matter comprising sea cucumber lipid fractions with no carotenoid material obtained by the following methods:
    a. contacting red carotenoid-bearing sea cucumber lipid fraction with activated clay or similar suitable material or material which adsorbs the pigments
    b. separating such activated clay from remaining lipid fraction solution which is essentially free of carotenoids.

12. A method of obtaining an essentially odorless and tasteless proteinaceous sea cucumber gut meal which is dry and free of lipid fractions obtained by extracting sea cucumber gut material with solvents to remove total lipids, and drying residue to less than 10% moisture.

13. A composition of matter consisting of dry proteinaceous de-lipidized gut material of the sea cucumber *Cucumaria frondosa* extracted by the following methods:
    a. extracting guts from sea cucumber organism and drying such sea cucumber gut material
    b. extraction of lipid fractions by means of solvent
    c. drying of solvent free material.

* * * * *